(12) United States Patent
Komoto et al.

(10) Patent No.: US 10,188,308 B2
(45) Date of Patent: Jan. 29, 2019

(54) METHOD OF IDENTIFYING THE SPATIAL DISTRIBUTION OF AREAS IN A SENSORY AREA OF BRAIN, PROGRAM, AND RECORDING MEDIUM THEREFOR

(71) Applicant: CANON KABUSHIKI KAISHA, Tokyo (JP)

(72) Inventors: Atsushi Komoto, Moriya (JP); Yoshikatsu Ichimura, Tokyo (JP); Yasuhiro Kawashima, Tokyo (JP); Jungo Miyazaki, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 885 days.

(21) Appl. No.: 14/294,706

(22) Filed: Jun. 3, 2014

(65) Prior Publication Data
US 2014/0371573 A1 Dec. 18, 2014

(30) Foreign Application Priority Data
Jun. 13, 2013 (JP) ................. 2013-124442

(51) Int. Cl.
| | | |
|---|---|---|
| *A61B 5/05* | (2006.01) | |
| *A61B 5/0484* | (2006.01) | |
| *A61B 5/055* | (2006.01) | |
| *A61B 5/00* | (2006.01) | |

(52) U.S. Cl.
CPC ...... *A61B 5/04842* (2013.01); *A61B 5/04845* (2013.01); *A61B 5/055* (2013.01); *A61B 5/4064* (2013.01); *A61B 5/0075* (2013.01)

(58) Field of Classification Search
None
See application file for complete search history.

(56) References Cited

U.S. PATENT DOCUMENTS

| | | | | |
|---|---|---|---|---|
| 2002/0038294 A1* | 3/2002 | Matsugu | ............ | G06K 9/00973 706/20 |
| 2005/0113680 A1* | 5/2005 | Ikeda | .................... | A61B 6/481 600/425 |
| 2007/0252595 A1* | 11/2007 | Volegov | ................. | A61B 5/055 324/307 |
| 2009/0318826 A1* | 12/2009 | Green | .................... | A61B 5/048 600/545 |

(Continued)

OTHER PUBLICATIONS

Wilkinson et al (The effects of stimulus symmetry on landmark judments in left and right visual fields).*

(Continued)

*Primary Examiner* — Joel F Brutus
(74) *Attorney, Agent, or Firm* — Venable LLP

(57) ABSTRACT

A method of identifying a spatial distribution of areas includes: a first step of determining a rough spatial distribution of at least one area in a sensory area of cerebral cortex in each of a left hemisphere and right hemisphere of the brain that is a target area of the identification; a second step of applying a sensory stimulus to the identification target area; a third step of obtaining brain activity information; and a fourth step of using the brain activity information to calculate one of a coefficient of cross-correlation, and coherence, between brain activity information of areas, assessing synchrony between the left and right hemispheres, and changing the spatial distribution determined in the first step.

24 Claims, 5 Drawing Sheets

(56) References Cited

U.S. PATENT DOCUMENTS

2011/0028827 A1\* 2/2011 Sitaram ................ A61B 5/0059
                                                          600/410
2012/0302867 A1\* 11/2012 Ichimura .............. A61B 5/0484
                                                          600/409

OTHER PUBLICATIONS

Druker et al (Spatial probability aids visual stimulus discrimination).\*
Portocello et al. (Eds.), "Visual Cortex: New Research," New York: Nova Science Publishers, Inc., Chapter 4, pp. 195-226 (2008).
Wandell et al., "Visual Field Maps in Human Cortex," Neuron Review, vol. 56, pp. 366-383 (2007).

\* cited by examiner

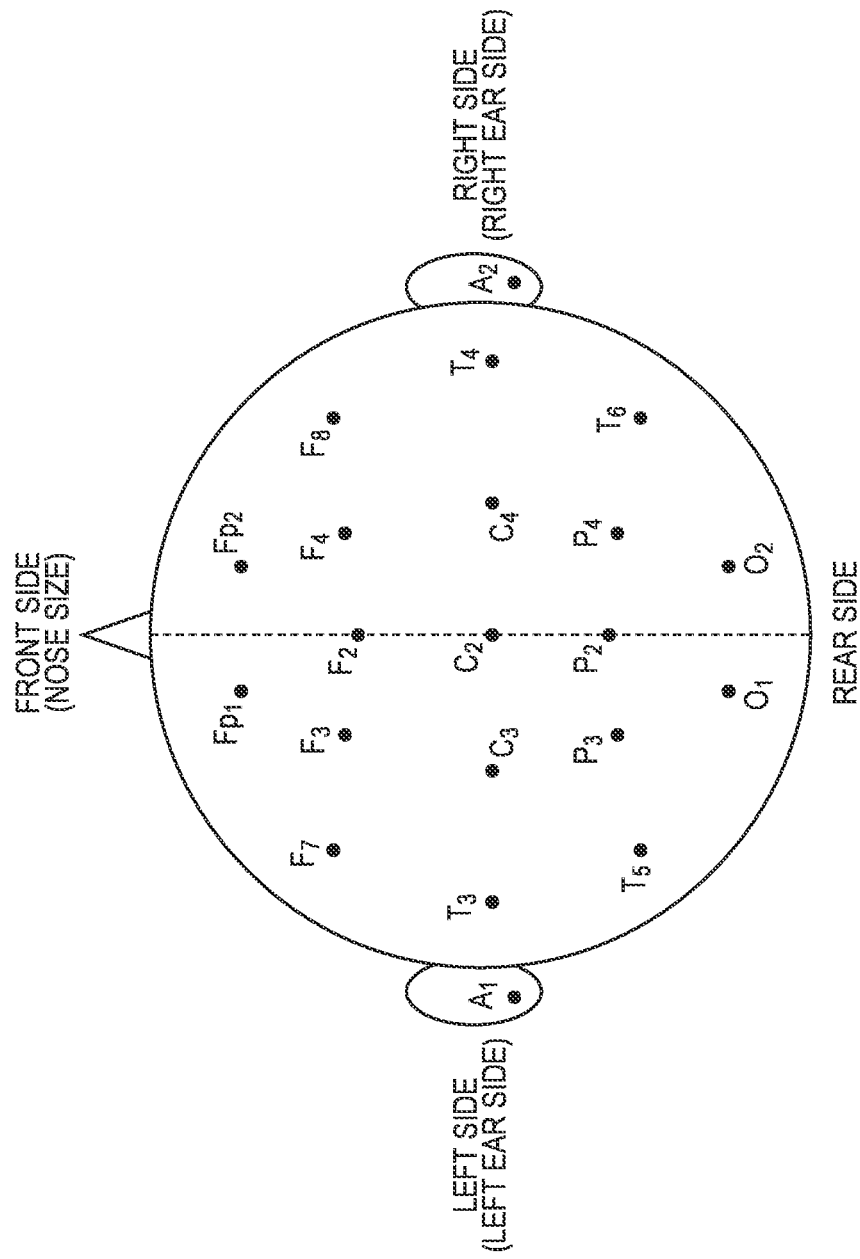

METHOD OF IDENTIFYING THE SPATIAL DISTRIBUTION OF AREAS IN A SENSORY AREA OF BRAIN, PROGRAM, AND RECORDING MEDIUM THEREFOR

BACKGROUND OF THE INVENTION

Field of the Invention

The present invention relates to a method of identifying the spatial distribution of areas in a sensory area of brain, a program, and a recording medium therefor.

Description of the Related Art

The brains of humans and apes have sensory areas which respectively handle processing of visual, auditory, and other sensory functions. It has been found that some sensory areas can be divided into finer function sites (areas), and attempts are being made to identify the locations and shapes of those areas in order to assess human senses quantitatively. The locations and shapes of areas that form a sensory area of brain are hereinafter referred to as the spatial distribution of areas.

This sensory area model in which a sensory area is divided into areas is called retinotopy in the case of visual sense and tonotopy in the case of auditory sense, and researches about visual sense which is the most important sense are being particularly actively carried out. Areas are identified by presenting a specific sensory stimulus to a subject (human, ape, or the like), and obtaining and analyzing information on brain activity that is observed in response to the stimulus, as disclosed in Wandell, B. A., Dumoulin, S. O., & Brewer, A. A., (2007), "Visual Field Maps in Human Cortex", Neuron, V. 56, pp. 366-383, and Portcello, T. A., & Velloti, R. B., (Eds.), (2008), "Visual Cortex: New Research", New York: Nova Science Publishers.

However, existing methods of identifying the spatial distribution of areas have the following problems.

Only a limited few types of sensory stimuli are used in the identification of the spatial distribution of areas, thereby limiting the amount of brain activity information to be analyzed for the identification of the spatial distribution of areas as well. In addition, there are no quantitative criteria at the stage where the obtained brain activity information is analyzed and areas are identified, thus necessitating manual determination by those who have considerable experience.

The existing methods also need to use a stimulus to one sensory area at a time, for example, a visual stimulus alone or an auditory stimulus alone.

SUMMARY OF THE INVENTION

The present invention has been made in view of the problems described above, and an object of the present invention is therefore to provide a method of identifying the spatial distribution of areas in a sensory area of brain, a program, and a recording medium therefore with which more types of sensory stimuli than in the past can be used to obtain brain activity information, the identification of areas does not require considerable experience, and using a stimulus to one sensory area at a time is not a necessary condition.

According to one embodiment of the present invention, there is provided a method of identifying a spatial distribution of areas in a sensory area of brain by obtaining brain activity information from a living body to which a sensory stimulus is applied, including: a first step of determining a rough spatial distribution of at least one area in a sensory area of cerebral cortex in each of a left hemisphere and right hemisphere of the brain that is a target area of the identification; a second step of applying a sensory stimulus to the identification target area; a third step of obtaining brain activity information by measuring brain activity in a region that includes the identification target area while the sensory stimulus is being applied in the second step; and a fourth step of using the brain activity information obtained in the third step to calculate one of a coefficient of cross-correlation, and coherence, between brain activity information of an area in the left hemisphere and brain activity information of an area in the right hemisphere which is of the same type as the area in the left hemisphere, assessing synchrony between the left and right hemispheres of the brain with the one of the following cross-correlation coefficient and the following coherence as a quantitative index, and changing the spatial distribution determined in the first step in a manner that increases the one of the coefficient of cross-correlation, and coherence, between brain activity information of the area in the left hemisphere and brain activity information of the area in the right hemisphere which is of the same type as the area in the left hemisphere.

Further, according to one embodiment of the present invention, there is provided a method of identifying a spatial distribution of areas in a sensory area of brain by obtaining brain activity information from a living body to which a sensory stimulus is applied, including: a first step of determining a rough spatial distribution of at least one area in a sensory area of cerebral cortex in each of a left hemisphere and right hemisphere of the brain that is a target area of the identification; a second step of applying a sensory stimulus to the identification target area; a third step of obtaining brain activity information by measuring brain activity in a region that includes the identification target area while the sensory stimulus is being applied in the second step; and a fourth step of using the brain activity information obtained in the third step to calculate one of a coefficient of cross-correlation, and coherence, between brain activity information of an area in the left hemisphere and brain activity information of an area in the right hemisphere, assessing synchrony between the left and right hemispheres of the brain with the one of the following cross-correlation coefficient and the following coherence as a quantitative index, and changing the spatial distribution determined in the first step in a manner that increases the one of the coefficient of cross-correlation, and the coherence, between brain activity information of the area in the left hemisphere and brain activity information of the area in the right hemisphere which is of the same type as the area in the left hemisphere, and decreases one of a coefficient of cross-correlation, and coherence, between brain activity information of one type of area in the left hemisphere and brain activity information of another type of area in the right hemisphere.

Further, according to one embodiment of the present invention, there is provided a program for causing a computer to execute steps including the first step to the fourth step in the above-mentioned methods of identifying a spatial distribution of areas in a sensory area of brain.

Further, according to one embodiment of the present invention, there is provided a computer-readable recording medium having recorded thereon the above-mentioned program.

Further features of the present invention will become apparent from the following description of exemplary embodiments with reference to the attached drawings.

BRIEF DESCRIPTION OF THE DRAWINGS

FIG. 3 is a schematic view illustrating how electrodes of an electroencephalograph are arranged in the embodiments of the present invention in conformity with the international ten-twenty electrode system.

DESCRIPTION OF THE EMBODIMENTS

Preferred embodiments of the present invention will now be described in detail in accordance with the accompanying drawings.

Described next are configuration examples of methods of identifying the spatial distribution of areas in a sensory area of brain according to embodiments of the present invention. However, the present invention is not limited in any way by these embodiments.

Figure 1B:
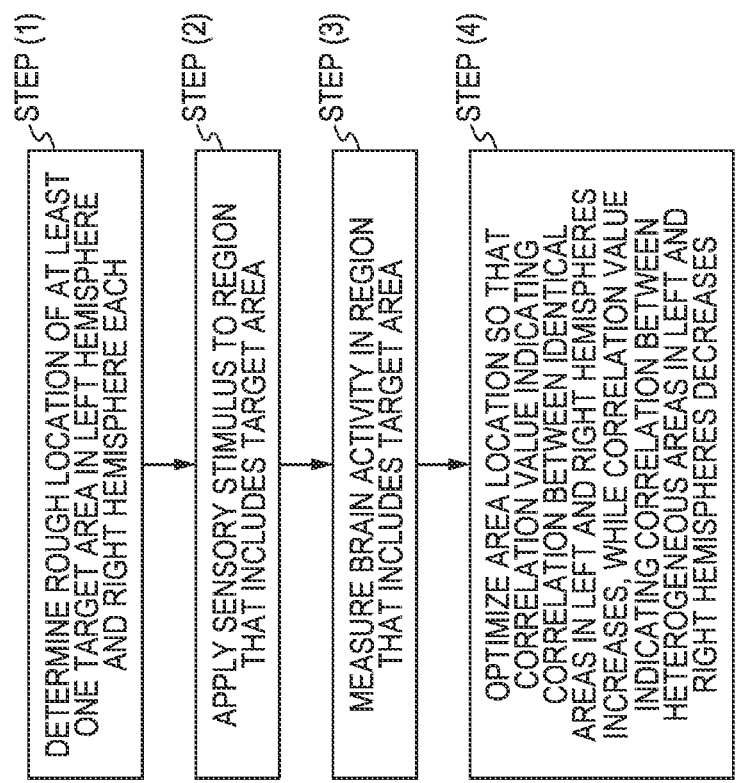
FIGS. 1A and 1B are diagrams illustrating methods of identifying the spatial distribution of areas in a sensory area of brain according to embodiments of the present invention.
Figure 1A:
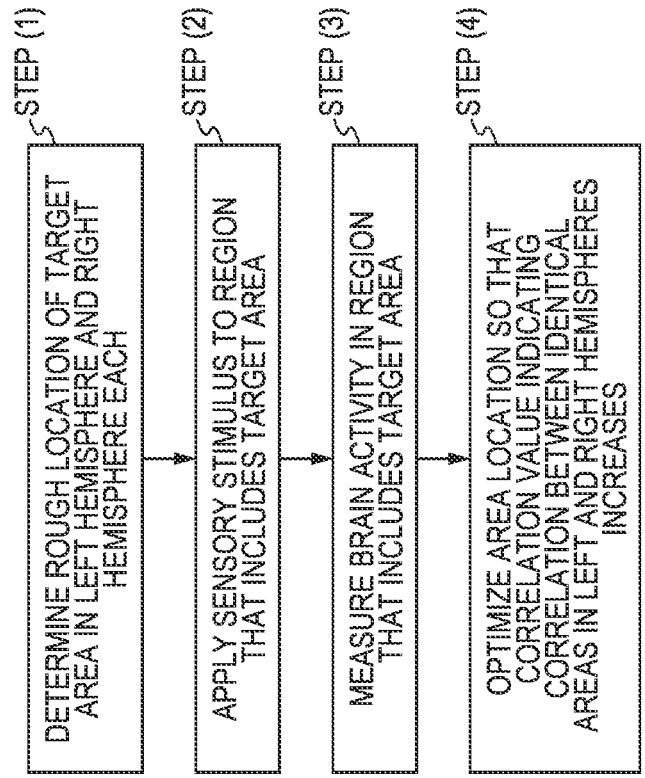

The method of identifying the spatial distribution of areas according to a first embodiment of the present invention is carried out via steps illustrated in FIG. 1A.

Specifically, in the first embodiment, the identification of the spatial distribution of areas that form a sensory area based on brain activity information obtained from a living body to which a sensory stimulus has been applied is conducted via the following first step (1) to fourth step (4).

(1) A first step of determining the rough spatial distribution of at least one area in a sensory area of cerebral cortex in the left hemisphere and the right hemisphere each.

(2) A second step of applying a sensory stimulus to the area.

(3) A third step of measuring brain activity in a region including the area that is observed while the sensory stimulus is applied.

(4) A fourth step of changing the area spatial distribution in a manner that increases a coefficient of cross-correlation, or coherence, between brain activity information of the area in the left hemisphere and brain activity information of the area in the right hemisphere which is of the same type as the area in the left hemisphere.

Further, the method of identifying the spatial distribution of areas according to a second embodiment of the present invention is carried out via steps illustrated in FIG. 1B.

Specifically, in the second embodiment, the identification of the spatial distribution of areas that form a sensory area based on brain activity information obtained from a living body to which a sensory stimulus has been applied is conducted via the following first step (1) to fourth step (4).

(1) A first step of determining the rough spatial distribution of at least one area in a sensory area of cerebral cortex in the left hemisphere and the right hemisphere each.

(2) A second step of applying a sensory stimulus to the area.

(3) A third step of measuring brain activity in a region including the area that is observed while the sensory stimulus is applied.

(4) A fourth step of changing the area spatial distribution in a manner that increases a coefficient of cross-correlation, or coherence, between brain activity information of the area in the left hemisphere and brain activity information of the area in the right hemisphere which is the same type as the area in the left hemisphere, and decreases a coefficient of cross-correlation, or coherence, between brain activity information of one type of area in the left hemisphere and brain activity information of another type of area in the right hemisphere.

The only difference between the first embodiment and the second embodiment is the fourth step. The first step to the third step which are common to the first embodiment and the second embodiment both are therefore described first in detail below. However, the first embodiment and the second embodiment vary from each other in that at least one target area is processed in the first embodiment whereas at least two target areas are processed in the second embodiment.

(1) About the First Step

In this step, the rough spatial distribution of a target area is determined by using one of, or a combination of, existing and known methods of determining an area.

For example, the rough spatial distribution of the area is determined by one of, or a combination of, existing and known methods that use a sensory stimulus such as the one disclosed in Wandell, B. A., Dumoulin, S. O., & Brewer, A. A., (2007), "Visual Field Maps in Human Cortex", Neuron, V. 56, pp. 366-383, one of, or a combination of, existing and known methods that are based on anatomical information such as the ones disclosed in Wandell, B. A., Dumoulin, S. O., & Brewer, A. A., (2007), "Visual Field Maps in Human Cortex", Neuron, V. 56, pp. 366-383 and Portcello, T. A., & Velloti, R. B., (Eds.), (2008), "Visual Cortex: New Research", New York: Nova Science Publishers, or a method that refers to the Brodmann's brain map, which is mentioned later.

The spatial distribution of the area determined here does not need to be finely accurate because the spatial distribution of the area is modified in the fourth step. The first step can therefore be performed even by those who do not have much experience.

(2) About the Second Step

A sensory stimulus is applied to a sensory area of a living body (for example, human body), such as visual cortex, auditory cortex, or vestibular cortex, that includes the target area by presenting an image or sound to the living body, giving acceleration to the living body, or the like.

(3) About the Third Step

Brain activity is measured in a region that includes at least one area (described below) out of the sensory area while a sensory stimulus is being applied in the second step.

In the case where an image is presented in the second step, for example, brain activity increases in the visual cortex of the living body. Brain activity can be measured via action potentials of neurons in the brain, or an electromagnetic field or a cerebral blood flow that is caused by the action potentials.

(4) About the Fourth Step

The fourth step in the first embodiment is described first.

Brain activity information of the area determined in the first step is extracted from each of the left hemisphere and the right hemisphere of the brain. A coefficient of cross-correlation, or coherence (herein, a cross-correlation coefficient and coherence may collectively be referred to as correlation value), between brain activity information of the area in the left hemisphere and brain activity information of the area in the right hemisphere which is of the same type as the area in the left hemisphere is used as a quantitative index to assess synchrony in brain activity information between the left hemisphere and the right hemisphere.

Synchrony in brain activity information is high between areas of the same type which process the same sensory information.

Accordingly, brain activity information of the area determined in the first step is extracted from each of the left hemisphere and the right hemisphere of the brain, and the area spatial distribution determined in the first step is changed into an optimum spatial distribution by changing the spatial distribution in a manner that increases the cross-correlation coefficient or the coherence.

The fourth step in the second embodiment is described next.

Brain activity information of the area determined in the first step is extracted from each of the left hemisphere and the right hemisphere of the brain. A coefficient of cross-correlation, or coherence between brain activity information of the area in the left hemisphere and brain activity information of the area in the right hemisphere is used as a quantitative index to assess synchrony in brain activity information between the left hemisphere and the right hemisphere.

Synchrony in brain activity information is high between areas of the same type which process the same sensory information.

On the other hand, synchrony in brain activity information is low between different types of areas which process different types of sensory information. Accordingly, the area spatial distribution determined in the first step is changed into an optimum spatial distribution by changing the spatial distribution in a manner that increases the coefficient of cross-correlation, or coherence, between areas of the same type, and decreases the coefficient of cross-correlation, or coherence, between areas of different types.

The optimization of the area spatial distribution in the fourth step of the first embodiment and the fourth step of the second embodiment can use one of, or a combination of, existing and known optimization methods such as the least square method and Newton's method.

With the area identification methods of the first embodiment and the second embodiment which use a quantitative index in the form of a cross-correlation coefficient or coherence in the fourth step, areas can be identified without requiring considerable experience.

The definitions of terms in the embodiments of the present invention, such as sensory area, area, left hemisphere, right hemisphere, sensory stimulus, living body, brain activity information, visual cortex, auditory cortex, and vestibular cortex, are described in detail below.

(Sensory Area)

A sensory area is a particular part of the cerebral cortex of brain that processes information (stimulus) from a sensory organ such as eyes or ears. Examples of sensory areas include visual cortex which processes visual information, auditory cortex which processes audio information, and vestibular cortex which processes the sense of balance.

(Area)

An area herein is one of finer function sites into which a sensory area is divided. Some sensory areas cannot be divided into multiple areas, and a sensory area as such is regarded as consisting of a single area.

A sensory area model in which visual cortex is divided into areas and a sensory area model in which auditory cortex is divided into areas are called retinotopy and tonotopy, respectively, and many findings about the two have been reported. These are described later concretely.

(Left Hemisphere, Right Hemisphere)

The left hemisphere and the right hemisphere herein mean the left brain and the right brain, respectively. Sensory areas as well as areas that have the same kind of information processing function are found in the left hemisphere and the right hemisphere both. However, those identical sensory areas and identical areas generally process different spatial ranges. For instance, the visual cortex in the left hemisphere mainly processes the right visual field whereas the visual cortex in the right hemisphere mainly processes the left visual field.

(Sensory Stimulus)

A sensory stimulus in the embodiments of the present invention is not limited to particular stimuli as long as the stimulus changes brain activity in a subject's sensory area such as visual cortex, auditory cortex, or vestibular cortex.

Examples of a sensory stimulus include a visual stimulus which changes brain activity in the visual cortex such as an image, an auditory stimulus which changes brain activity in the auditory cortex such as a sound, an audio-visual stimulus which changes brain activity in the visual cortex and the auditory cortex such as an image with a sound, and an vestibular stimulus which changes brain activity in subject's vestibular cortex by giving acceleration to the subject via a roller coaster or the like.

The sensory stimulus used may be a stimulus that changes brain activity in one type of sensory area or a stimulus that changes brain activity in multiple types of sensory areas at the same time.

Flight simulators, for instance, present a visual stimulus and a vestibular stimulus at the same time to a living body.

Movies and other sensory stimuli that contain images and sounds both are sensory stimuli that present a visual stimulus and an auditory stimulus at the same time.

The embodiments of the present invention use a visual stimulus to identify an area in the visual cortex and use an auditory stimulus to identify an area in the auditory cortex.

Areas in multiple types of sensory areas can be identified simultaneously by presenting a stimulus that changes brain activity in multiple types of sensory areas, such as the flight simulators and movies described above.

In order to execute the first step of the embodiments of the present invention, it is preferred to present to a subject one of existing and known sensory stimuli for identifying an area.

Examples of preferred visual stimuli include those disclosed in Wandell, B. A., Dumoulin, S. O., & Brewer, A. A., (2007), "Visual Field Maps in Human Cortex", Neuron, V. 56, pp. 366-383: one is "eccentricity" in which a ring-shaped pattern spreads cyclically from the central visual field, and another is "angle" in which a wedge-shaped pattern rotates cyclically about the central visual field. The first step of the embodiments of the present invention is executed by presenting a preferred visual stimulus and analyzing resultant data.

This is because a large amount of findings has been accumulated about area identifying methods that use those visual stimuli.

However, determining an area with precision solely by the first step of the embodiments of the present invention requires considerable experience. The embodiments of the present invention therefore later change and optimize the spatial distribution of the area in the fourth step of the first embodiment and the fourth step of the second embodiment by using a cross-correlation coefficient or coherence of an area in the left hemisphere and an area in the right hemisphere as a quantitative index.

It is also preferred to present a sensory stimulus that is specialized to the function of an area whose spatial distribution is to be identified.

For example, in the case where the target area is one of MT and MST areas in the visual cortex, which are described later and known to be areas that process visual information of a moving object and the like, it is preferred to present a visual stimulus that is kinetic.

In the case where the target area is the V8 area in the visual cortex which is described later and known to be an area that processes visual information related to colors, it is preferred to present a visual stimulus that is full of color information.

It is preferred for a sensory stimulus that is used in the fourth step of the embodiments of the present invention to obtain brain activity information to be symmetrical with respect to central visual field of the subject as much as possible.

For example, an image symmetrical with respect to the central visual field of the subject is preferred in the case of a visual stimulus, and a sound from sources symmetrically arranged with respect to center of the subject's ears is preferred in the case of an auditory stimulus.

This is because, in the fourth step of the embodiments of the present invention, the spatial distribution of an area in the left hemisphere and an area in the right hemisphere is changed by focusing attention on the value of a cross-correlation coefficient or coherence of the areas.

The reason is that, in the visual cortex, for example, where the left hemisphere generally processes visual information of the right visual field and the right hemisphere generally processes visual information of the left visual field, synchrony between the left and the right is poor when the right field and left field of a visual stimulus differ significantly from each other, which makes it difficult to use a cross-correlation coefficient or coherence as an index for area identification.

The present invention is less limited than Wandell, B. A., Dumoulin, S. O., & Brewer, A. A., (2007), "Visual Field Maps in Human Cortex", Neuron, V. 56, pp. 366-383 in the type of sensory stimuli that can be used.

The only restriction in the present invention with regard to what sensory stimuli can be used is, as described above, that the anisotropy of the sensory stimulus not be too great. The area spatial distribution identification of the present invention can therefore use the value of a coefficient of cross-correlation, or coherence, between an area in the left hemisphere and an area in the right hemisphere with regard to brain activity information that is obtained in response to different types of sensory stimuli.

This means that areas can be identified at a higher precision as brain activity information obtained in response to a sensory stimulus to a target sensory area increases in count and volume through mechanical learning of the brain activity information.

The present invention is also capable of simultaneously identifying the spatial distribution of areas that respectively form multiple sensory areas by using a sensory stimulus that stimulates multiple types of sensory areas.

(Living Body)

A living body in this embodiment means an animal with brain such as a human (human body), an ape, or a dog. A living body preferred in the information obtaining methods according to the embodiments of the present invention is a human body.

A case where the living body used is a human body is described below. A living body is also referred to as subject herein.

(Brain Activity Information)

Brain activity in the embodiments of the present invention is brain activity response of a living body to the sensory stimulus described above. Brain activity response can be quantified by measuring changes in the action potentials of neurons in the brain, or changes in electromagnetic field or changes in cerebral blood flow those are caused by the action potential changes.

Action potentials of neurons in the brain can be measured with a nerve action recording machine which uses electrodes. Changes in electromagnetic field that are caused by action potential changes can be measured with an electroencephalograph or a magnetoencephalograph.

Changes in cerebral blood flow that are caused by action potential changes can be measured with a functional magnetic resonance imaging (fMRI) machine, an NIRS machine, or a positron emission tomography (PET) machine.

Because these machines each have strengths and limitations, one can choose a machine that is suitable for his/her purpose. For example, fMRI machines are capable of measuring brain activity information at a relatively high spatial resolution but are rather low in temporal resolution.

Electroencephalographs, on the other hand, are superior in temporal resolution but inferior in spatial resolution to fMRI machines. Electroencephalographs and NIRS machines are less expensive, and are capable of providing brain activity information safely without constraining a subject much. With electroencephalographs and NIRS machines, however, it is difficult to obtain brain activity information in the interior of the brain (for example, a part where the left hemisphere and the right hemisphere abut each other). When brain activity information in the interior of the brain is to be obtained, fMRI machines and the like are suitable.

Brain activity information in the embodiments of the present invention means data measured by measurement of the brain activity described above and information that is obtained by processing the data suitably. An example of brain activity information is information about a visual stimulus.

Information about a visual stimulus can be obtained from such data as changes in the action potentials of neurons in a subject's brain that are observed when a visual stimulus is presented to the subject, or changes in electromagnetic field or changes in cerebral blood flow that are caused by the action potential changes.

When brain activity information is processed, it is preferred to process measurement data of brain activity suitably so that information about the target sensory stimulus is extracted.

For example, data measured with an fMRI machine, which is used in the following description as an instrument for measuring brain activity, contains noise generated by the machine, the subject's pulses and breathing, and other types of information irrelevant to brain activity response to a sensory stimulus which is the target. Those components can be removed by linear trend removal (detrend), a frequency response filter, or the like.

(Visual Cortex)

In the embodiments of the present invention, visual sense is a sense in which visible light is a physical input, and visual information refers to information about the color, shape, motion, texture, depth, and the like of an external object, information about the category of an object, and spatial information of the environment such as the positional relation between objects. Visual cortex is a sensory area related to visual sense.

Visual cortex which is known to be breakable into multiple areas is one of targets to classify the areas in assessment methods according to the embodiments of the present invention.

Some of those known areas are the primary visual area (V1 (V1d and V1v)), the secondary visual area (V2 (V2d and V2v), the tertiary visual area (V3 and V3A), the quaternary visual area (V4 (V4d and V4v)), the middle temporal area (MT area), the middle superior temporal area (MST area), the septenary visual area (V7, also called IPS-0), the ventral posterior area (VP area, also called V3v), the lateral occipital area (LO area), and the octonary visual area (V8).

The MT area and the MST area may collectively be referred to as MT+ area.

Multiple classification systems have been proposed for area classification in the visual cortex, particularly in a region that includes a high-order area.

For instance, there are other classification systems for the areas corresponding to V4v and V8, and one of the systems proposes to classify the areas into hV4, V01, and V02.

The areas corresponding to V4d and the LO area also have other classification systems, and one of the systems proposes to classify the areas into V3B, LO1, and LO2.

These areas are referred to herein by the notation that uses "V4v" and "V8" or the notation that uses "V4d" and "LO area".

Visual information is processed by the visual cortex which has been confirmed to be located in the occipital lobe, a part of the parietal lobe, and a part of the temporal lobe.

The cerebral cortex has the frontal lobe which is located at the front, the occipital lobe which is located at the rear, the parietal lobe which is located at the top, and the temporal lobe which is located on the side.

Figure 2B:
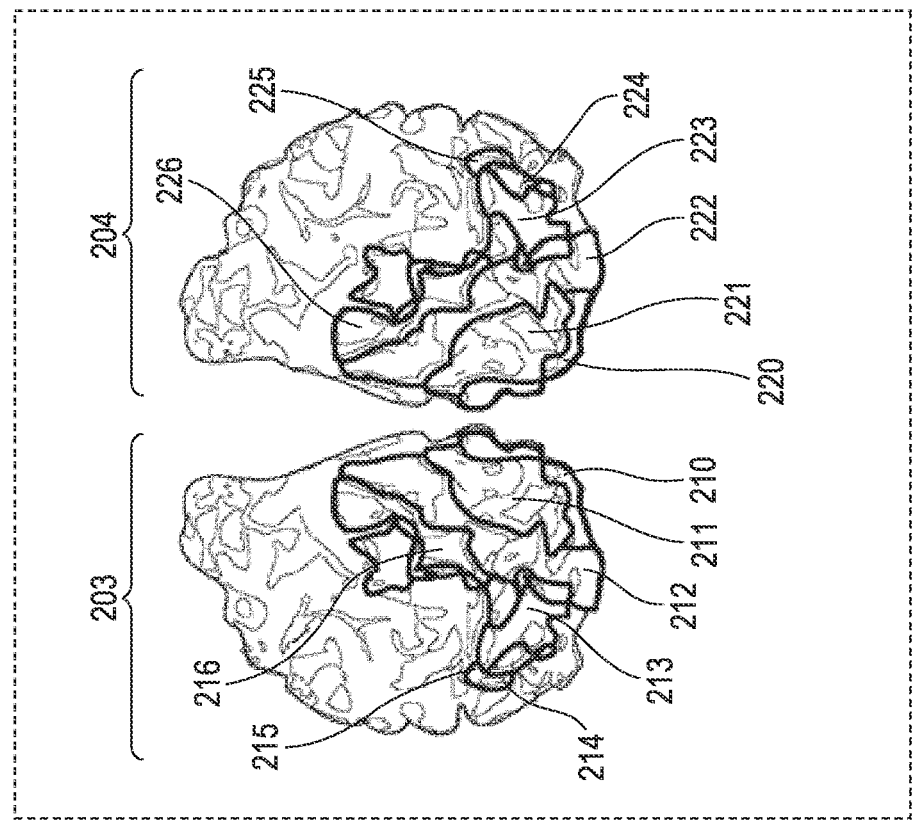
FIGS. 2A and 2B are diagrams illustrating the left and right hemispheres of a cerebrum which are actually connected by a corpus callosum are separated for convenience' sake.
Figure 2A:
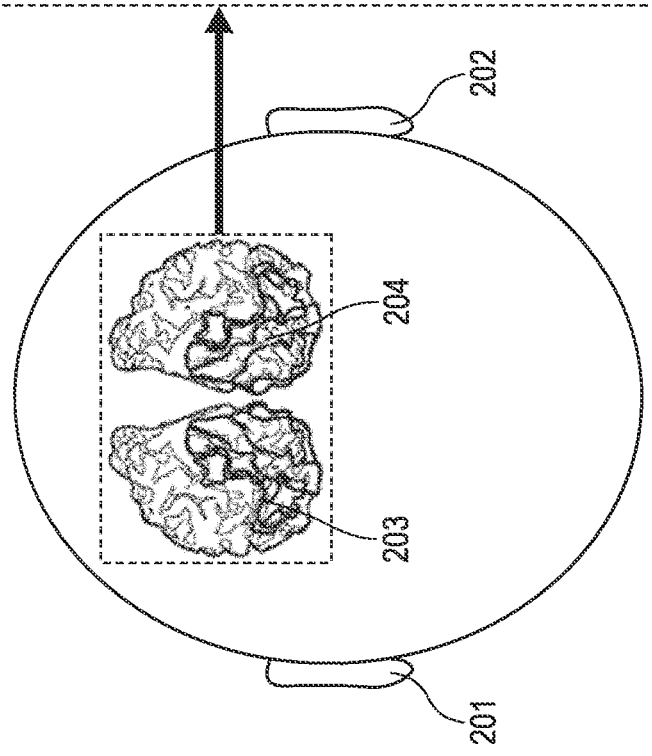

FIGS. 2A and 2B are diagrams in which the left and right hemispheres of a cerebrum which are actually connected by a corpus callosum are separated for convenience's sake.

FIG. 2A is a schematic view of the surface of the cerebral cortex viewed from the occipital side.

FIG. 2B is an enlarged view of the cerebral cortex surface of FIG. 2A.

Areas described below are arranged as illustrated in FIGS. 2A and 2B in a subject who has normal visual cortex, although there are slight individual differences. This arrangement may therefore be referred to when the first step of the identification methods of the present invention is executed in the case of the visual cortex.

In FIG. 2A, the left ear is denoted by 201, the right ear is denoted by 202, the left cerebral hemisphere is denoted by 203, and the right cerebral hemisphere is denoted by 204.

The left cerebral hemisphere 203 includes V1 (V1v and V1d) 210, V2 (V2v and V2d) 211, V3 212, an LO area 213, an MT area 214, an MST area 215, and V3A 216 (FIG. 2B).

The right cerebral hemisphere 204 includes V1 (V1v and V1d) 220, V2 (V2v and V2d) 221, V3 222, an LO area 223, an MT area 224, an MST area 225, and V3A 226 (FIG. 2B).

As illustrated in FIG. 2B, visual cortexes are positioned substantially symmetrically in the left and right hemispheres. Visual information is first input to the visual areas V1 of the left and right hemispheres which are located at the rear end of the occipital lobe. The visual information is then processed in the visual areas that handle higher-order information such as V2, V3, and V3A.

The visual areas V1, V2, and V3 are located roughly in Area 17, Area 18, and Area 19, respectively, in the Brodmann's brain map.

As disclosed in Wandell, B. A., Dumoulin, S. O., & Brewer, A. A., (2007), "Visual Field Maps in Human Cortex", Neuron, V. 56, pp. 366-383 and Portcello, T. A., & Velloti, R. B., (Eds.), (2008), "Visual Cortex: New Research", New York: Nova Science Publishers, the rough spatial distribution of visual areas can be determined also from an anatomical standpoint.

For instance, the rough spatial distribution of V1 ranges outward from a sulcus in the occipital that is called a calcarine sulcus and reaches the surrounding gyrus. The rough spatial distribution of V8 is in a fusiform gyrus in the ventral region of the occipital of the brain.

The first step of the identification methods of the present invention can be executed also by using one of, or a combination of, such existing and known anatomical findings.

Visual information processing subsequent to V1 and V2 in the visual cortex roughly branches into two streams. One is a visual information processing path that is called a dorsal pathway and passes through areas that run along the dorsal cerebral cortex, such as V3, V3A, the MT area, the MST area, and the LO area.

A large number of neurons that respond to visual motion and to a binocular disparity is found in the dorsal pathway, and are considered to be involved in the recognition of the spatial arrangement of self and others, the kinetic state, shapes, and the like. The other stream is a visual information processing path that is called a ventral pathway and passes through areas that run along the ventral cerebral cortex, such as the ventral quaternary visual area (V4v) and the octonary visual area (V8). A large number of neurons that respond to color and the like is found in the ventral pathway, and are considered to be involved in the recognition of colors in the visual system.

In the case where activity in the visual cortex is measured with an electroencephalograph (EEG), V1, V2, V3, and other areas that are distributed at the entrance of the visual cortex can be detected as signals of electrodes O1 and O2 in the international ten-twenty electrode system because the areas are located at the backmost part of the occipital lobe. Areas that are distributed in the parietal lobe such as V3A and V7 can be detected as signals of electrodes P2, P3, and P4 in the international ten-twenty electrode system. The area V4d, the MT area, the MST area, and the LO area which are distributed in the temporal lobe can be detected as signals of electrodes T5 and T6 in the international ten-twenty electrode system.

The international ten-twenty electrode system is an international standard system for determining the placement of measurement electrodes in a head when brain activity is measured with an electroencephalograph.

FIG. 3 is a diagram illustrating the placement of electrodes in the international ten-twenty electrode system. In the case of measuring brain activity in V1, V2, V3, and other similar areas with an electroencephalograph, for example, electrodes are placed at O1 and O2 in FIG. 3.

While using the electrode arrangement in the international ten-twenty electrode system in the first step of determining the rough distribution of an area is a standard in the present invention, the electrode arrangement in the first step is not limited to a particular arrangement.

As described later, the electrode arrangement is adjusted (the fourth step) and the spatial distribution of the target area is identified in a manner that optimizes the value of a coefficient of cross-correlation, or coherence, between brain activity of the target area in the left hemisphere and brain activity of the target area in the right hemisphere.

(Auditory Cortex)

In the embodiments of the present invention, auditory sense is a sense in which a sound is a physical input, and audio information means sound intensity, pitch, tone timbre, the direction of the source of the sound, rhythm, pronunciation, and the like.

Auditory cortex is a sensory area in the cerebral cortex related to auditory sense.

Auditory cortex includes primary, secondary, and tertiary auditory areas which are located in Area 41 and Area 42 in Brodmann's brain map. Activity in the auditory cortex measured with an electroencephalograph can be detected as signals of electrodes T3 and T4 in the international ten-twenty electrode system.

While using the electrode arrangement in the international ten-twenty electrode system in the first step of determining the rough distribution of an area is a standard in the present invention, the electrode arrangement in the first step is not limited to a particular arrangement.

As described later, the electrode arrangement is adjusted (the fourth step) and the spatial distribution of the target area is identified in a manner that optimizes the value of a coefficient of cross-correlation, or coherence, between brain activity of the target area in the left hemisphere and brain activity of the target area in the right hemisphere.

(Vestibular Cortex)

Sense of balance in the embodiments of the present invention is a sense in which information about a subject's sense of balance (information such as how far the human body is tilted or how fast the living body is moving) is a physical input.

Vestibular cortex is a sensory area in the cerebral cortex related to sense of balance.

The vestibular cortex is defined in the embodiments of the present invention as being located near the temporoparietal junction, which connects the parietal lobe and the temporal lobe at the posterior of the lateral sulcus. Activity in the vestibular cortex when measured with an electroencephalograph can be detected as signals of electrodes T3, T4, P3, and P4 in the international ten-twenty electrode system.

While using the electrode arrangement in the international ten-twenty electrode system in the first step of determining the rough distribution of an area is a standard in the present invention, the electrode arrangement in the first step is not limited to a particular arrangement.

As described later, the electrode arrangement is adjusted (the fourth step) and the spatial distribution of the target area is identified in a manner that optimizes the value of a coefficient of cross-correlation, or coherence, between brain activity of the target area in the left hemisphere and brain activity of the target area in the right hemisphere.

Machines used to measure brain activity in the embodiments of the present invention, such as an electroencephalograph, an NIRS machine, and an fMRI machine, are described next in detail taking the visual cortex as an example. These machines can similarly be used for the measurement of other sensory areas such as the auditory cortex and the vestibular cortex.

(Electroencephalograph)

An electroencephalograph in the embodiments of the present invention measures an electromagnetic field that is caused by action potentials of neurons in the brain.

Exploring electrodes are attached to a subject's scalp and fluctuations in electric potential from a reference electrode which has an electric potential of 0 (usually an electrode attached to an ear lobe) are measured as time-series data.

Brain waves of the subject are measured while the sensory stimulus described above is presented to the subject.

For example, in the case where an image that plays and pauses repeatedly at regular time intervals is used as a sensory stimulus, action potentials of neurons in the visual cortex increase and electroencephalographic signals increase as well when the image plays, compared to when the image pauses.

When the image plays and pauses repeatedly at regular time intervals, electroencephalographic signals in the visual cortex repeatedly increase and attenuate in step with the playing and pausing. In other words, when a repetition frequency of the playing and pausing of the sensory stimulus is applied as f, the waveform of measured electroencephalographic signals approaches the waveform of the sine wave of the frequency f.

Using an electrode arrangement that conforms to the international ten-twenty electrode system in brain wave measurement in the first step is a standard here, but the present invention is not limited thereto.

FIG. 3 is a schematic view illustrating the placement of electrodes of an electroencephalograph that conforms to the international ten-twenty electrode system. FIG. 3 is a top view of the head of a viewer 1, and the upper part, lower part, left part, and right part of FIG. 3 respectively illustrate the front side (nose side), the rear side (occipital side), the left side (left ear side), and the right side (right ear side).

The electrodes are denoted by A1, A2, O1, O2, P2, P3, P4, C2, C3, C4, F2, F3, F4, T3, T4, T5, T6, F7, F8, Fp1, and Fp2.

The electrodes A1 and A2 are called reference electrodes, and are attached typically near ear lobes where the electric potential can be deemed as 0. The rest of the electrodes are called exploring electrodes, and detect changes in electric potential with respect to the reference electrodes as electroencephalographic signals.

The electrodes O1 and O2 detect brain waves of the occipital, P2, P3, and P4 detect brain waves of the parietal, C2, C3, and C4 detect brain waves of the central part, T3, T4, T5, and T6 detect brain waves of the temporal, and F2, F3, F4, F7, F8, Fp1, and Fp2 detect brain waves of the frontal.

Brain waves can be measured at a higher spatial resolution than in the international ten-twenty electrode system by increasing the count or density of electrodes.

With the spatial resolution improved, identifying the spatial distribution of a target area more accurately is facilitated and the present invention can thus be carried out favorably.

In the embodiments of the present invention, the electrode arrangement determined in the first step is modified based on a quantitative assessment that uses the cross-correlation coefficient or coherence of the fourth step to identify the spatial distribution of a target area.

(NIRS Machine)

Near infrared spectroscopy (NIRS) machines are for measuring changes in cerebral blood flow that are considered to be caused by changes in neuron activity. A possible process through which changes in neuron activity cause changes in cerebral blood flow is as follows.

Neurons consume oxygen when changing activity, which temporarily creates an oxygen-depleted state.

In order to resolve this situation, blood is pumped into cerebral blood vessels around the oxygen-depleted neurons and the neurons are supplemented with oxygen. An NIRS machine is an instrument of brain activity measurement for measuring changes in the volume of cerebral blood flow, or changes in the proportion of oxygenated hemoglobin and reduced hemoglobin that are contained in the cerebral blood flow.

A light transmitting probe and light receiving probe of an NIRS machine are attached to the surface of a subject's head.

The light transmitting probe irradiates the interior of the subject's brain with near-infrared light, and the near-infrared light irradiating the interior of the subject's brain is reflected by the cerebral cortex or the like and returns to the head surface to be detected with the light receiving probe.

Oxygenated hemoglobin and reduced hemoglobin that are contained in cerebral blood flow have different light absorption spectra from each other with respect to light in the near-infrared wavelength range. The near-infrared light radiated from the light transmitting probe is absorbed by the oxygenated hemoglobin and reduced hemoglobin that are contained in cerebral blood flow. The amount of light detected by the light receiving probe is therefore reduced by an amount that reflects the content of the oxygenated hemoglobin and reduced hemoglobin.

The volume of cerebral blood flow at a site through which the near-infrared light has passed and the proportion of oxygenated hemoglobin and reduced hemoglobin that are contained in cerebral blood flow can accordingly be estimated from a change in the amount of light between the time of irradiation and the time of detection. By measuring over time the change in the amount of light, changes with time in the amount of cerebral blood flow at the irradiated site and changes with time of the proportion of oxygenated hemoglobin and reduced hemoglobin that are contained in cerebral blood flow can be recorded as time-series brain activity data.

Cerebral blood flow can be measured at a higher spatial resolution by increasing the count or density of light receiving probes.

With the spatial resolution improved, identifying the spatial distribution of a target area more accurately is facilitated and the present invention can thus be carried out favorably.

In the embodiments of the present invention, the light receiving probe arrangement determined in the first step is modified based on a quantitative assessment that uses the cross-correlation coefficient or coherence of the fourth step to identify the spatial distribution of a target area.

(fMRI Machine)

An fMRI machine is an MRI machine that visualizes hemodynamic response related to brain activity.

In the case where dynamic cerebral blood flow is measured with the use of an fMRI machine, brain activity is visualized usually by identifying a site that has responded to a sensory stimulus through statistical processing or the like, and displaying the identified site as a color map on an anatomical image.

The machine configuration of fMRI machines differs from that of NIRS machines. However, fMRI machines and NIRS machines have in common that the measurement target is a change in cerebral blood flow and that data can be used in area identification. A description on the fMRI machine configuration is therefore omitted here.

In NIRS machines, however, received light whose spectrum is observed is a reflection of near-infrared light that has been emitted from a probe at the head surface and reflected at the surface of the cerebrum.

NIRS machines therefore can only detect cerebral blood flow information of the vicinity of the head surface. In contrast, fMRI machines are capable of detecting changes in electromagnetic field that are caused by changes in blood flow as electromagnetic waves, and are accordingly superior in that changes in cerebral blood flow can be measured throughout the brain (including the interior of the brain).

(Cross-Correlation Coefficient, Coherence)

A cross-correlation coefficient in the embodiments of the present invention is an index that is quantified similarity between two pieces of time-series data.

For example, two pieces of time-series data are each converted into a vector. Normalization of the vector is performed so that an average value of all elements of the vector is 0 and that the magnitude of the vector is 1, and then the inner product of the two vectors is used as a cross-correlation coefficient.

Figure 4:
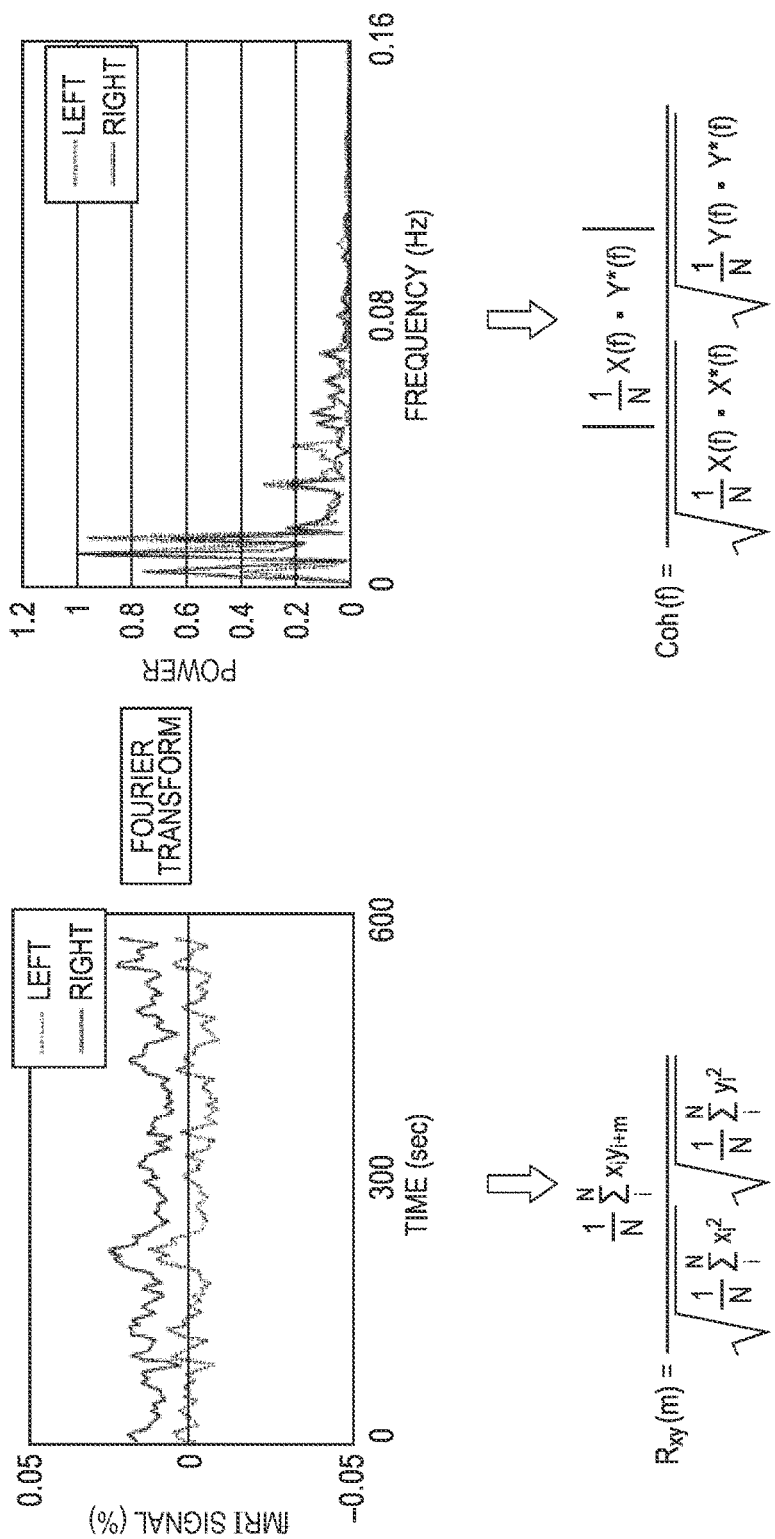
FIG. 4 is a diagram illustrating brain activity information and expressions for calculating a cross-correlation coefficient or coherence, between brain activity information of the area in the left hemisphere and brain activity information of the area in the right hemisphere according to the embodiments of the present invention.

A cross-correlation coefficient is obtained generally by an expression shown in the left part of FIG. 4. The cross-correlation coefficient used in the embodiments of the present invention is calculated by setting 0 to m in the expression and thus eliminating a time lag (a delay in time).

In the information obtaining methods according to the embodiments of the present invention, a cross-correlation coefficient of time-series data about brain activity is obtained by, for example, the following method.

(i). Data is obtained by subtracting, from every element of brain activity time-series data $(x1, x2, \ldots, xn)$ of one brain region which is obtained in the third step described above, an average value $x'$ of the elements.

(ii). The square root of the square sum of the elements obtained in (i) is calculated.

(iii). The data (i) is divided by the value calculated in (ii).

(iv). The same steps as (i) to (iii) are executed for brain activity time-series data $(y1, y2, \ldots, yn)$ of another brain region which is obtained in the third step.

(v). The inner product of (iii) and (iv) is calculated.

Obtaining a cross-correlation coefficient through Steps (i) to (v) corresponds to calculating the expression of FIG. 4 by substituting $(x1, x2, \ldots, xn)$ and $(y1, y2, \ldots, yn)$ in the expression with measured brain activity data.

FIG. 4 also includes a flow chart that illustrates a concrete method of calculating a correlation value of brain activity time-series data. The correlation value used in the embodiments of the present invention is one of a cross-correlation coefficient in the temporal domain and coherence in the frequency domain.

Shown in FIG. 4 as an example are brain activity time-series data of the primary visual area (V1) in the left hemisphere and brain activity time-series data of the primary visual area (V1) in the right hemisphere which are detected by a functional magnetic resonance imaging machine (the left graph of FIG. 4).

In the left graph of FIG. 4, the dotted line represents the brain activity time-series data of V1 in the left hemisphere and the solid line represents brain activity time-series data of V1 in the right hemisphere.

To calculate a cross-correlation coefficient which is the correlation value in the temporal domain, the brain activity time-series data of V1 in the left and right hemispheres is substituted in a mathematical expression for calculating a cross-correlation coefficient that is defined by the expression illustrated in the lower left part of FIG. 4.

In the illustrated expression, $xi$ and $yi$ each represent time-series data, and $Rxy(m)$ represents a cross-correlation coefficient of $xi$ and $yi$. The symbol $m$ represents a lag between the two pieces of time-series data, and is set to 0 in the calculation according to the embodiments of the present invention.

To calculate coherence which is the correlation value of the frequency domain, the brain activity time-series data in the left graph of FIG. 4 is transformed by Fourier transform into power spectra illustrated in the right graph of FIG. 4. In the right graph of FIG. 4, the dotted line represents a power spectrum calculated from the brain activity time-series data of V1 in the left hemisphere, and the solid line represents a power spectrum calculated from the brain activity time-series data of V1 in the right hemisphere.

The coherence is calculated by substituting the power spectra into a mathematical expression that is defined by an expression illustrated in the lower right part of FIG. 4.

In the illustrated expression, X(f) and Y(f) represent Fourier transform of the time-series data xi and Fourier transform of the time-series data yi, respectively, X*(f) and Y*(f) represent a complex conjugate of X(f) and a complex conjugate of Y(f), respectively, and Coh represents coherence.

Because coherence is expressed as a frequency function, quantifying the degree of relevance between the two pieces of time-series data requires deriving an arbitrary index from the coherence. An average value in the coherence can be given as an example. Other indices that are derived from the coherence can also be used. An index derived in the manner described above is also referred to as coherence in the embodiments of the present invention.

In the embodiments of the present invention, excluding brain activity information (time-series data) that is obtained immediately after a sensory stimulus is presented to the subject from the calculation of the cross-correlation coefficient or the coherence is preferred in some cases.

This is because brain activity information obtained immediately after a sensory stimulus is presented is unstable.

For example, in the case where a sensory stimulus that lasts such as an image is presented to the subject, brain activity information about a change in sensory stimulus from an environment where no image is presented into an environment where an image is prevented may be measured immediately after the image is presented. This stems from the difficulty of measuring with clarity brain activity information about brain activity caused by the image which is the target.

When the cross-correlation coefficient or the coherence is close to 1, which is the theoretical maximum value, it means that brain activity information of the area determined in the first step has a time-series pattern that is similar between the left hemisphere and the right hemisphere, and that the correlation between the two is high.

In other words, areas of the same type are identified successfully and favorably. When cross-correlation coefficient or the coherence is much smaller than 1, on the other hand, brain activity information of the area determined in the first step has a time-series pattern that is not similar between the left hemisphere and the right hemisphere, and the correlation between the two is low. Therefore, areas of the same type are not identified favorably.

In this manner, by calculating a cross-correlation coefficient of brain activity information that is observed in a particular region of a subject's left hemisphere and right hemisphere each when a sensory stimulus is presented, the accuracy of the spatial distribution of the area can be assessed quantitatively from the magnitude of the cross-correlation coefficient.

For instance, when the cross-correlation coefficient or the coherence is much smaller than 1, the spatial distribution of the area needs to be modified suitably, and the work of modifying the spatial distribution is repeated until optimization is achieved.

Specifically, area identification as the one described below can be conducted. A visual stimulus such as an image is used as a sensory stimulus, and brain activity information is collected from the left hemisphere and the right hemisphere by measuring brain activity in a region that includes the part determined in the first step while the sensory stimulus is presented.

Steps (i) to (v) described above are executed for the brain activity data of the left hemisphere and the brain activity data of the right hemisphere to calculate the cross-correlation coefficient.

The cross-correlation coefficient is obtained by performing the same measurement on one subject with the use of multiple types of visual stimuli. The area spatial distribution is changed gradually so that the cross-correlation coefficient approaches the theoretical maximum value, 1, and the optimum area spatial distribution is thus determined.

In the present invention, an area can be identified also by the following method.

This method can be particularly effective for simultaneous identification of multiple types of areas.

As described above, areas of different types process different types of sensory stimulus information.

A coefficient of cross-correlation, or coherence, between one type of area in the left hemisphere and another type of area in the right hemisphere therefore has a value much smaller than the theoretical maximum value, 1.

Accordingly, a correlation value is calculated in the form of cross-correlation coefficient or coherence for every combination of an area in the left hemisphere and an area in the right hemisphere, and the spatial distribution of the areas is adjusted repeatedly through optimization in which increasing the correlation value for areas of the same type while decreasing the correlation value for areas of different types is used as an index.

This method allows the use of $N^2$ correlation values as indices for the identification of N areas, and can therefore identify areas by using a larger number of quantitative indices.

Some sensory areas are formed of multiple areas as described above, and there is no room for error in the basic arrangement relation between areas an example of which is illustrated in FIGS. 2A and 2B.

Departing significantly from findings about the anatomical features of areas also needs to be avoided.

In the case of the visual cortex, in particular, an area that should be in a ventral region must not be placed in a dorsal region, and an area that should be in a dorsal region must not be placed in a ventral region.

The present invention can be carried out more favorably by taking these constraints regarding the spatial distribution of areas into account when the spatial distribution of the areas is optimized based on the correlation value.

According to the embodiments of the present invention, the accuracy of the spatial distribution of areas can be assessed quantitatively and, if necessary, can be modified by calculating a cross-correlation coefficient or coherence in the manner described above. The optimization of the area spatial distribution can use one of, or a combination of, existing and known methods such as the least square method and Newton's method.

In addition, because the embodiments of the present invention use a coefficient of cross-correlation, or coherence, between brain activity information of the left hemisphere and brain activity information of the right hemisphere which is a quantitative assessment index, area identification according to the embodiments of the present invention does not require considerable experience.

The embodiments of the present invention can also use more diverse sensory stimuli than in the past to obtain brain activity information, and area identification can thus be performed based on a huge amount of brain activity information.

Moreover, areas in multiple types of sensory areas can be identified simultaneously by using brain activity information that is obtained when multiple types of sensory areas are stimulated at the same time.

In another embodiment of the present invention, the following program which controls a computer so that the computer executes the first step to the fourth step can be configured, and a computer-readable recording medium on which this program is recorded can be configured.

(Program)

As an example of the program according to this embodiment, a program for executing steps including the first to fourth steps of the first and second embodiments described above can be configured that identifies areas of a living body to which a sensory stimulus has been applied.

The program according to this embodiment may be recorded on a recording medium or may be downloaded from the Internet. The program is designed to be readable by machines such as a computer.

(Recording Medium)

As an example of the recording medium according to this embodiment, a recording medium readable by machines such as a computer can be configured to record a program for executing the first to fourth steps of the first and second embodiments described above that is a program for identifying areas of a living body to which a sensory stimulus has been applied.

Examples of the recording medium include CDs (CD-R, CD-RW, and the like), DVDs (DVD-R, DVD-RW, and the like), flash memories, hard disks, magnetic tapes, and floppy (trademark) disks.

EXAMPLES

Examples of the present invention are described below. However, the present invention is not in any way limited by these Examples.

Example 1

A configuration example of a method of identifying the spatial distribution of areas in a sensory area of brain to which the present invention is applied is described as Example 1.

Specifically, an example is described in which the spatial distribution of V8 in the visual cortex which is the target area is identified by measuring brain activity with an fMRI machine and using an image as a sensory stimulus.

In this example, V8 which is located roughly in a fusiform gyrus in the ventral region of the occipital of the brain is the area to be identified.

The first step in the present invention described above is executed by determining the rough spatial distribution of V8 based on a subject's MRI anatomical image (T1 image) which is taken in advance and the anatomical findings described above.

The brain activity measuring machine used in this example is an fMRI machine.

A display device has a screen which is provided in a tubular measurement part of the fMRI machine and a video projector which is set up outside the measurement part and which projects an image onto the screen. The video projector is controlled with the use of a control computer.

Figure 5:
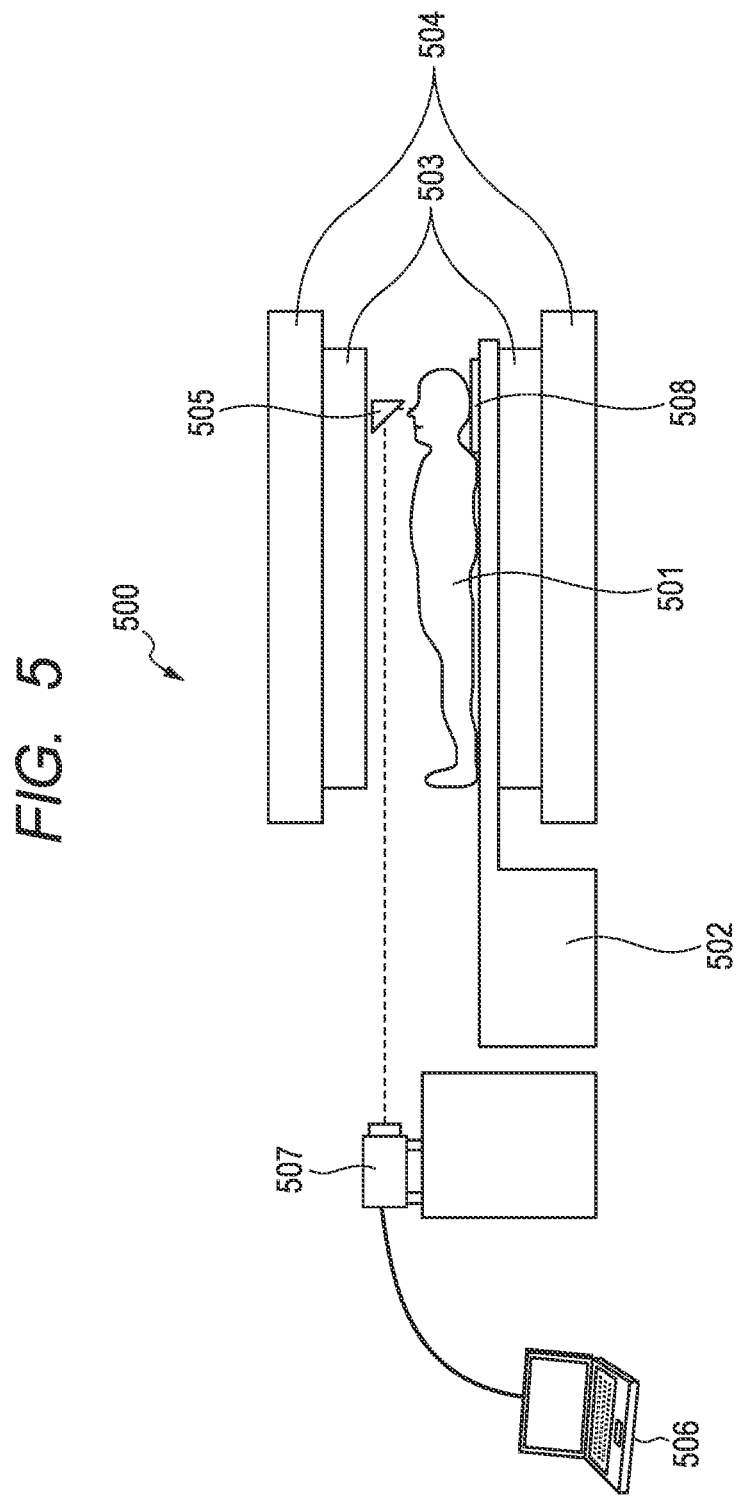
FIG. 5 is a diagram illustrating an fMRI machine and a visual stimulus presenting method that is used in Examples of the present invention.

FIG. 5 is a sectional view of the fMRI machine that is used in this example.

In FIG. 5, the fMRI machine is denoted by 500. A viewer 501 lies on a bed 502, which is an accessory of the fMRI machine 50, and is put in a tubular measurement part within which a gradient coil 503 and a superconductive magnet 504 are provided.

A screen 505 is provided inside the measurement part in front of the face of the viewer 501. A video projector 507 controlled by a control computer 506 projects an image onto the screen 505 from outside the measurement part.

A signal detecting coil 508 is placed at the back of the head of the viewer 501 to detect electromagnetic wave signals correlated to changes in cerebral blood flow that accompany neuron activity.

A color motion image shot with a video camera is used as a sensory stimulus.

In order to improve the symmetry of the image, the shot color image (image A1) is reduced, and a color image (image A8) is created from a square of eight reduced images A1 by eight reduced images A1. Brain activity of the subject when this visual stimulus is applied is measured.

Time-series data of brain activity measured by the fMRI machine 500 is analyzed on a computer with the use of a program.

Specifically, the color image A8 is used to optimize the spatial distribution of V8 as follows.

Before the correlation value about correlation between the left hemisphere and the right hemisphere is calculated, noise originating from the fMRI machine and other components irrelevant to the visual stimulus are removed in preprocessing.

The expression in the lower left part of FIG. 4 (m=0) is used to calculate a coefficient of cross-correlation between brain activity time-series data in the left hemisphere and brain activity time-series data in the right hemisphere for V8 whose rough spatial distribution has been determined.

The spatial distribution of V8 is changed so that the cross-correlation coefficient increases, while satisfying constraints such as that the rough distribution of V8 is in a fusiform gyrus in the ventral region and that V8 abuts on V4v. As a result, the value of the cross-correlation coefficient has increased from (0.75) to (0.80) and it has also been confirmed that V8 of the left hemisphere and the V8 of the right hemisphere are each in a fusiform gyrus of the ventral region. The spatial distribution of V8 is thus identified more accurately.

When a color image that is similar to the image A8 but is a shot of a different subject is used to optimize the spatial distribution of V8 in the manner described above, substantially the same spatial distribution is obtained.

Performing the above-described work with the use of multiple pieces of brain activity data which are obtained by switching images increases the number of quantitative indices even more. The spatial distribution of V8 can therefore be identified more accurately.

In the case where the image A1 is used as a visual stimulus, on the other hand, the cross-correlation coefficient is only (0.76) even after the optimization of the spatial distribution of V8, and there is little synchrony in brain activity between the left hemisphere and the right hemisphere. This proves that a highly anisotropic image is not desirable as a sensory stimulus.

Example 2

A configuration example in which the spatial distribution of a target area that is a combined area of the MT area and the MST area (hereinafter referred to as MT+ area) is identified by measuring brain activity with an electroencephalograph and using an image as a sensory stimulus is described as Example 2.

Specifically, this example discusses an example in which the MT+ area located roughly in an inferior temporal sulcus in the dorsal region of the occipital of the brain is an area to be identified.

In this example, the first step in the present invention is executed by determining the rough spatial distribution of the MT+ area based on brain activity information that is measured with the use of the visual stimulus "eccentricity" and "angle" described above and an fMRI machine, and based on anatomical information (findings).

The brain activity measuring machine used in this example is an electroencephalograph. The spatial distribution of the MT+ area determined in the first step substantially coincides with the positions of T5 and T6 in the international ten-twenty electrode system, and electrodes of the electroencephalograph are placed on the subject's head at T5 and T6.

The subject who is standing watches the image A8 of Example 1 that is displayed on a liquid crystal display under control of a computer. Time-series data of brain activity of the subject watching the image is measured with the electroencephalograph.

The time-series data of the brain activity measured with the electroencephalograph is analyzed on a computer with the use of a program.

Before the correlation value about correlation between the left hemisphere and the right hemisphere is calculated, noise originating from the electroencephalograph and other components irrelevant to the visual stimuli are removed in preprocessing.

An average value of coherence of brain activity time-series data in the left and right hemispheres is calculated for the MT+ area whose rough spatial distribution has been determined as an average of the expression in the lower right part of FIG. 4.

The positions of the electrodes placed at T5 and T6 are changed so that the average value of the coherence increases.

As a result, the average value of the coherence has increased and it has also been confirmed that the MT+ area of the left hemisphere and the MT+ area of the right hemisphere are each in the dorsal region. The spatial distribution of the MT+ area is thus identified more accurately.

When a similar color image that is a shot of a different subject is used to optimize the spatial distribution of the MT+ area in the manner described above, substantially the same electrode positions are obtained. Performing the above-described work with the use of multiple pieces of brain activity data which are obtained by switching images increases the number of quantitative indices even more. The spatial distribution of the MT+ area can therefore be identified more accurately.

In the case where the image A1 is used as a visual stimulus, on the other hand, the average value of the coherence after the optimization of the spatial distribution of the MT+ area is smaller than when the image A8 is used, and there is little synchrony in brain activity between the left hemisphere and the right hemisphere. This proves that a highly anisotropic image is not desirable as a sensory stimulus.

Example 3

A configuration example in which the spatial distribution of a target area that is the MT+ area and the LOc area is identified by measuring brain activity with an fMRI machine and using an image as a sensory stimulus is described as Example 3.

The area to be identified in this example is the MT+ area, which is located roughly in an inferior temporal sulcus in the dorsal region of the occipital of the brain, and the LOc area, which is further at the back of the occipital and abuts on the MT+ area. The first step is executed by determining rough spatial distribution of the MT+ area and the LOc area based on brain activity information that is measured with the use of the visual stimuli "eccentricity" and "angle" described above and an fMRI machine.

In the same system as in Example 1, time-series data of brain activity is measured with the fMRI machine.

The time-series data of the brain activity measured with the fMRI machine is analyzed on a computer with the use of a program.

Before the correlation value about correlation between the left hemisphere and the right hemisphere is calculated, noise originating from the fMRI machine and the like, which are irrelevant to the visual stimuli, are removed in preprocessing.

The expression in the lower left part of FIG. 4 (m=0) is used to calculate a cross-correlation coefficient of every combination of brain activity time-series data in the left hemisphere and brain activity time-series data in the right hemisphere for the LOc area and the MT+ area whose rough spatial distribution has been determined.

The spatial distribution of the LOc area and the MT+ area is changed so that the coefficient of cross-correlation between the LOc area in the left hemisphere and the LOc area in the right hemisphere, as well as the coefficient of cross-correlation between the MT+ area in the left hemisphere and the MT+ area in the right hemisphere, increases, and that the coefficient of cross-correlation between the LOc area in the left hemisphere and the MT+ area in the right hemisphere, as well as the coefficient of cross-correlation between the MT+ area in the left hemisphere and the LOc area in the right hemisphere, decreases, while satisfying constraints such as that the rough distribution of the MT+ area is in a fusiform gyrus in the dorsal region and that the LOc area abuts on the MT+ area.

As a result, the value of each cross-correlation coefficient has changed as shown in FIGS. 1A and 1B, and it has also been confirmed that the MT+ area is in a fusiform gyrus of the dorsal region, and that the LOc area abuts on the MT+ area. The spatial distribution of the MT+ area and the LOc area is thus identified more accurately.

When a color image that is similar to the image A8 but is a shot of a different subject is used to optimize the spatial distribution of the MT+ area and the LOc area in the manner described above, substantially the same spatial distribution is obtained.

Performing the above-described work with the use of multiple pieces of brain activity data which are obtained by switching images increases the number of quantitative indices even more. The spatial distribution of the MT+ area and the LOc area can therefore be identified more accurately.

TABLE 1

| Two areas for which cross-correlation coefficient is calculated | Cross-correlation coefficient (before optimization) | Cross-correlation coefficient (after optimization) |
| --- | --- | --- |
| LOc of left hemisphere and LOc of right hemisphere | 0.85 | 0.87 |
| MT+ area of left hemisphere and MT+ area of right hemisphere | 0.88 | 0.90 |
| LOc of left hemisphere and MT+ area of right hemisphere | 0.75 | 0.73 |
| MT+ area of left hemisphere and LOc of right hemisphere | 0.83 | 0.82 |

The area identification methods according to the present invention which are capable of assessing a sense of a living body quantitatively can be applied not only to medical uses but also to product assessment and the like.

The present invention realizes a method of identifying the spatial distribution of areas in a sensory area of brain, a program, and a recording medium therefore with which more types of sensory stimuli than in the past can be used to obtain brain activity information, the identification of areas does not require considerable experience, and using a stimulus to one sensory area at a time is not a necessary condition.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-124442, filed Jun. 13, 2013, which is hereby incorporated by reference herein in its entirety.

What is claimed is:

1. A method of identifying a spatial distribution of areas in a sensory area of brain by obtaining brain activity information from a human body of a subject to which a sensory stimulus is applied, comprising:
   determining a rough spatial distribution of at least one target area in a sensory area of cerebral cortex in each of a left hemisphere and right hemisphere of the brain;
   applying a sensory stimulus to the target area by showing a video to the subject;
   obtaining brain activity information using a brain activity measuring machine which measures brain activity in a region that includes the target area while the sensory stimulus is being applied to the target area;
   calculating a correlation value between brain activity information of the target area in the left hemisphere and brain activity information of the target area in the right hemisphere using the obtained brain activity information; and
   adjusting the determined rough spatial distribution of the target area to an adjusted spatial distribution of the target area in each of the left and right hemispheres so that the correlation value between brain activity information of respective target areas of an identical type in the adjusted spatial distribution in the left and right hemispheres increases.

2. The method of identifying a spatial distribution of areas in a sensory area of brain according to claim 1, wherein the sensory area comprises any one of visual cortex, auditory cortex, and vestibular cortex.

3. The method of identifying a spatial distribution of areas in a sensory area of brain according to claim 1, wherein the fourth step comprises a step of changing the spatial distribution determined in the first step by using multiple pieces of the brain activity information.

4. The method of identifying a spatial distribution of areas in a sensory area of brain according to claim 1, wherein the sensory stimulus comprises a sensory stimulus that is symmetrical with respect to the human body.

5. The method of identifying a spatial distribution of areas in a sensory area of brain according to claim 1, wherein the sensory stimulus comprises any one of a visual stimulus which changes brain activity in visual cortex, an auditory stimulus which changes brain activity in auditory cortex, an audio-visual stimulus which changes brain activity in the visual cortex and the auditory cortex, and a vestibular stimulus which changes brain activity in vestibular cortex.

6. The method of identifying a spatial distribution of areas in a sensory area of brain according to claim 1, wherein in obtaining the brain activity information, the brain activity is measured by using any one of an action potential change of the brain of the human body, a change caused in electromagnetic field by the action potential change, and a change caused in cerebral blood flow by the action potential change.

7. The method of identifying a spatial distribution of areas in a sensory area of brain according to claim 1, wherein the first step comprises a step of determining the rough spatial distribution of the identification target area based on anatomical information.

8. The method of identifying a spatial distribution of areas in a sensory area of brain according to claim 1, wherein the first step comprises a step of determining the rough spatial distribution of the identification target area based on brain activity information that is obtained with use of a visual stimulus in which a ring-shaped pattern spreads cyclically from a central visual field, and a visual stimulus in which a wedge-shaped pattern rotates cyclically about the central visual field.

9. The method of identifying a spatial distribution of areas in a sensory area of brain according to claim 1, wherein in the fourth step comprises a step of changing the spatial distribution determined in the first step by optimizing a value of the coefficient of cross-correlation between brain activity information of one area and brain activity information of another area based on multiple pieces of brain activity information which are obtained with use of the sensory stimulus in multitudes.

10. The method of identifying a spatial distribution of areas in a sensory area of brain according to claim 1, wherein the third step comprises a step of measuring the brain activity by using a functional magnetic resonance imaging machine (fMRI machine) and using an image as a sensory stimulus.

11. The method of identifying a spatial distribution of areas in a sensory area of brain according to claim 1, wherein the third step comprises a step of measuring the brain activity by using an electroencephalograph and using an image as a sensory stimulus.

12. The method of identifying a spatial distribution of areas in a sensory area of brain according to claim 1, wherein the correlation value includes one of a coefficient of cross-correlation and coherence.

13. A method of identifying a spatial distribution of areas in a sensory area of brain by obtaining brain activity information from a human body of a subject to which a sensory stimulus is applied, comprising:
  determining a rough spatial distribution of at least one target area in a sensory area of cerebral cortex in each of a left hemisphere and right hemisphere of the brain;
  applying a sensory stimulus to the target area by showing a video to the subject;
  obtaining brain activity information using a brain activity measuring machine which measures brain activity in a region that includes the target area while the sensory stimulus is being applied to the target area;
  calculating a correlation value between brain activity information of the target area in the left hemisphere and brain activity information of the target area in the right hemisphere using the obtained brain activity information; and
  adjusting the determined rough spatial distribution of the target area to an adjusted spatial distribution of the target area in each of the left and right hemispheres so that a first correlation value between brain activity information of respective target areas of an identical type in the adjusted spatial distribution in the left and right hemispheres increases and a second correlation value between brain activity information of respective target areas of different types in the adjusted spatial distribution in the left and right hemispheres increases.

14. The method of identifying a spatial distribution of areas in a sensory area of brain according to claim 13, wherein the sensory area comprises any one of visual cortex, auditory cortex, and vestibular cortex.

15. The method of identifying a spatial distribution of areas in a sensory area of brain according to claim 13, wherein the fourth step comprises a step of changing the spatial distribution determined in the first step by using multiple pieces of the brain activity information.

16. The method of identifying a spatial distribution of areas in a sensory area of brain according to claim 13, wherein the sensory stimulus comprises a sensory stimulus that is symmetrical with respect to the human body.

17. The method of identifying a spatial distribution of areas in a sensory area of brain according to claim 13, wherein the sensory stimulus comprises any one of a visual stimulus which changes brain activity in visual cortex, an auditory stimulus which changes brain activity in auditory cortex, an audio-visual stimulus which changes brain activity in the visual cortex and the auditory cortex, and a vestibular stimulus which changes brain activity in vestibular cortex.

18. The method of identifying a spatial distribution of areas in a sensory area of brain according to claim 13, wherein in obtaining the brain activity information, the brain activity is measured by using any one of an action potential change of the brain of the human body, a change caused in electromagnetic field by the action potential change, and a change caused in cerebral blood flow by the action potential change.

19. The method of identifying a spatial distribution of areas in a sensory area of brain according to claim 13, wherein the first step comprises a step of determining the rough spatial distribution of the identification target area based on anatomical information.

20. The method of identifying a spatial distribution of areas in a sensory area of brain according to claim 13, wherein the first step comprises a step of determining the rough spatial distribution of the identification target area based on brain activity information that is obtained with use of a visual stimulus in which a ring-shaped pattern spreads cyclically from a central visual field, and a visual stimulus in which a wedge-shaped pattern rotates cyclically about the central visual field.

21. The method of identifying a spatial distribution of areas in a sensory area of brain according to claim 13, wherein the fourth step comprises a step of changing the spatial distribution determined in the first step by optimizing a value of the coefficient of cross-correlation between brain activity information of one area and brain activity information of another area based on multiple pieces of brain activity information which are obtained with use of the sensory stimulus in multitudes.

22. The method of identifying a spatial distribution of areas in a sensory area of brain according to claim 13, wherein the third step comprises a step of measuring the brain activity by using a functional magnetic resonance imaging machine (fMRI machine) and using an image as a sensory stimulus.

23. The method of identifying a spatial distribution of areas in a sensory area of brain according to claim 13, wherein the third step comprises a step of measuring the brain activity by using an electroencephalograph and using an image as a sensory stimulus.

24. The method of identifying a spatial distribution of areas in a sensory area of brain according to claim 13, wherein the correlation values include one of a coefficient of cross-correlation and coherence.

* * * * *